United States Patent [19]
Johannssen et al.

[11] Patent Number: 5,294,539
[45] Date of Patent: Mar. 15, 1994

[54] NITRATE REDUCTASE FROM YEASTS, THE PREPARATION AND USE THEREOF

[75] Inventors: Walther Johannssen, Reinheim; Harry Schwartz, Hofheim-Diedenb.; Reiner Gromes, Gross-Umstadt.; Martin Heinrich, Darmstadt, all of Fed. Rep. of Germany

[73] Assignee: Merck Patent Gesellschaft mit beschrankter Haftung, Darmstadt, Fed. Rep. of Germany

[21] Appl. No.: 781,165

[22] PCT Filed: Feb. 2, 1991

[86] PCT No.: PCT/EP91/00199
§ 371 Date: Oct. 16, 1991
§ 102(e) Date: Oct. 16, 1991

[87] PCT Pub. No.: WO91/12319
PCT Pub. Date: Aug. 22, 1991

[30] Foreign Application Priority Data
Feb. 16, 1990 [DE] Fed. Rep. of Germany ....... 4004900

[51] Int. Cl.$^5$ .............. C12Q 1/26; C12Q 1/12; C12N 9/02; C12R 1/72
[52] U.S. Cl. .................. 435/25; 435/37; 435/71.1; 435/189; 435/814; 435/921; 435/930
[58] Field of Search .......... 435/25, 37, 921, 814, 435/189, 71.1, 930

[56] References Cited

U.S. PATENT DOCUMENTS
5,169,758  12/1992  Fischer et al. ................. 435/25

FOREIGN PATENT DOCUMENTS
244771  11/1987  European Pat. Off. .

OTHER PUBLICATIONS

Chem Abs 105 No. 25 221446p (Dec. 1986) Choudary et al. Abs of Microbiol 1986, 47 (192-193) 135-47.
Chem Abs 85 No. 19 139035p (Nov. 8, 1976) Choudary et al. Abs "Indian Acad. Sci" Sec B 1976 (83) 5 (185-95).

*Primary Examiner*—Herbert J. Lilling
*Attorney, Agent, or Firm*—Millen, White, Zelano & Branigan, P.C.

[57] ABSTRACT

The invention relates to NAD(P)H-dependent nitrate reductase from yeasts, to a process for the preparation thereof and to the use thereof in a reagent for determining nitrate. The nitrate reductase is characterized by a molecular weight of about 350 000 D and can be obtained by yeast cells which have been cultivated in a completely synthetic nutrient medium with nitrate as the sole nitrogen source and which contain nitrate reductase being disrupted in phosphate buffer, the crude extract being chromatographed on an anion exchanger, the fractions containing nitrate reductase being mixed with protein, concentrated by ultrafiltration and dried by fluidized bed granulation. The reagent for determining nitrate contains, besides the nitrate reductase prepared in this way, also NAD(P)H and a color reagent for determining nitrite.

11 Claims, No Drawings

NITRATE REDUCTASE FROM YEASTS, THE PREPARATION AND USE THEREOF

The invention relates to NAD(P)H-dependent nitrate reductase from yeasts, to a process for the preparation thereof and to the use thereof in a reagent for determining nitrate.

The quantitative determination of nitrate in a wide variety of samples, for example in water (mineral water, tap water, wastewater), foodstuffs (fruit, vegetables, beer, wine, juices, meat and meat products, milk and dairy products, baby food) and soil samples is becoming increasingly important. Nitrate determinations are extremely important, especially when there is suspicion of excessive concentrations injurious to health, in order to be able to prevent, for example, a potential carcinogenic nitrosamine formation.

Both physical (HPLC, gel chromatography) and chemical methods for determining the nitrate concentration are known. In the customary chemical methods, the nitrate is reduced to nitrite and the latter is detected by a diazotization reaction. These methods are very elaborate and cannot be used without problems for determinations in many organic materials.

EP 244 771 discloses a stabilized nitrate reductase and a reagent for determining nitrate using this nitrate reductase. The reagent contains, besides the enzyme and NAD(P)H, a zwitterionic buffer and a nitrogen heterocycle buffer. However, the enzyme has the disadvantage that its preparation is very elaborate, and that it shows an interfering nitrite reductase activity, which makes the described completely enzymatic nitrate determination difficult. In addition, it has emerged that the nitrate reductase described in EP 244 771 satisfactorily converts nitrate to nitrite only with the relatively costly NADPH, but not with NADH.

The object of the invention was to find and isolate a nitrate reductase which is stable enough, and with which it is possible, to determine nitrate accurately even in low concentrations with a simple, low-cost and rapid test.

It has emerged, surprisingly, that yeasts which are able to grow with nitrate as the sole nitrogen source in a completely synthetic nutrient medium under aerobic conditions have a nitrate reductase which can be isolated in a simple process and which can be stabilized. The nitrate reductase prepared in this way can be used in a nitrate determination which avoids the disadvantages of the known methods.

The invention relates to a NAD(P)H-dependent nitrate reductase which is characterized by a molecular weight in the native state of about 350 000 D and which can be obtained by yeast cells which have been cultivated in a completely synthetic nutrient medium with nitrate as the sole nitrogen source and which contain nitrate reductase of the EC 1.6.6.2 type being disrupted in phosphate buffer, pH 6.5–8.5, the crude extract being chromatographed on an anion exchanger, the fractions containing nitrate reductase being mixed with 10–50 % protein, concentrated by ultrafiltration and dried by fluidized bed granulation.

The invention also relates to a process for the preparation of a NAD(P)H-dependent nitrate reductase, which is characterized in that yeast cells which have been cultivated in a completely synthetic nutrient medium with nitrate as the sole nitrogen source are disrupted in phosphate buffer, pH 6.5–8.5, in the presence of a complexing agent, mercaptoethanol, FAD, potassium hexacyanoferrate and a protease inhibitor, after centrifugation the crude extract is directly chromatographed on an anion exchanger, the fractions containing nitrate reductase are mixed with 10–50 % protein, concentrated by ultrafiltration and dried by fluidized bed granulation, and to a reagent for determining nitrate which is characterized by a content of the nitrate reductase prepared in this way, NAD(P)H and a color reagent for determining nitrite.

Examples of yeasts suitable for the preparation of the NAD(P)H-dependent nitrate reductase according to the invention are those of the genera Candida, Hansenula and Williopsis, preferably the genera Candida and Hansenula and the organisms *Candida boidinii* (DSM 70 026), Hansenula ciferrii (DSM 70 780), Hansenula saturnus (DMS 70 278), especially *Candida boidinii*.

The nitrate reductase is prepared from cells which are grown in a completely synthetic nutrient medium with nitrate as the sole nitrogen source. The cells are disrupted in a glass bead mill in potassium phosphate buffer, in the presence of a complexing agent (for example EDTA), mercaptoethanol, flavin adenine dinucleotide (FAD), potassium hexacyanoferrate and a protease inhibitor (for example PMSF); it is also possible to employ other protease inhibitors known to the person skilled in the art. After disruption of the cells and removal of the cell detritus by centrifugation it is possible, surprisingly, to chromatograph the crude extract obtained in this way without previous nucleic acid precipitation or fractional protein precipitation on an anion exchanger material (for example a wide-pore, cross-linked vinyl polymer with grafted-on polycations and trimethylammoniummethyl groups such as Fractogel EMD TMAE-650) which has been equilibrated with potassium phosphate buffer. The active nitrate reductase is eluted with an increasing KCl gradient at about 140 mmol/l KCl. An addition, mentioned in the state of the art, of sugar or sugar alcohols is not necessary for enzyme stabilization during the purification. The fractions which contain nitrate reductase activity are combined, mixed with 10–50% bovine serum albumin or other proteins (for example collagen hydrolysates) and concentrated by ultrafiltration. The solution obtained in this way contains an average of 6–7 units of nitrate reductase/mg of protein and is subsequently dried by fluidized bed granulation.

The completely synthetic nutrient medium in which the microorganisms are grown contains essentially the following constituents:

0.04 g/l m-inositol,
1.0 g/l potassium dihydrogen phosphate,
1.0 g/l magnesium sulfate,
4.5 g/l potassium hydrogen tartrate,
1.5 g/l potassium nitrate,
20.0 g/l glucose.

The nitrate reductase prepared by the process described, especially one from *Candida boidinii*, has the following $K_M$ values:

| NADH | $7.2 \times 10^{-5}$ M |
|---|---|
| NADPH | $6.9 \times 10^{-5}$ M |
| KNO$_3$(NADH) | $4.0 \times 10^{-3}$ M |
| KNO$_3$(NADPH) | $4.0 \times 10^{-4}$ M. |

The pH optimum in phosphate buffer is 7.0 (NADH-dependent) or 7.1 (NADPH-dependent). The temperature optimum is 30° C. (NADH-dependent) and 25° C. (NADPH-dependent). The molecular weight in the native state, determined by gel permeation chromatography, is about 350 000 D. End-product inhibition by nitrite takes place in the case of the NADH-dependent nitrate reductase only up to 50%.

It has proved to be particularly advantageous to prepare the reagent according to the invention for determining nitrate by converting the enzyme into a stable dry form by spraying the solution onto preformed seeds and subsequently encapsulating with polyvinylpyrrolidone. The seeds can consist, for example, of mannitol, polyethylene glycol or polyvinylpyrrolidone (US 4,820,627). The enzyme granules prepared in this way are distinguished by very low residual moisture, good storage stability and very good solubility. User-friendliness is increased by tableting the granules with reproducibly adjustable enzyme activity per tablet. The enzyme preparation according to the invention is stable in 50 mmol/l potassium phosphate buffer, pH 7.0, at 25° C. for several hours. The nitrate reductase preparation in the form of granules has virtually unlimited stability on storage at −20° C.

This stabilized nitrate reductase is used to reduce nitrate to nitrite, and subsequently the resulting nitrite is determined in a chemical detection reaction by diazotization, for example with sulfanilic acid and N-naphthylethylenediammonium chloride at 540 or 525 rm. The reagent solutions necessary for the determination contain, apart from 0.1–1 U, preferably 0.7 U, of nitrate reductase, also 50–200 mmol/l, preferably 100 mmol/l, potassium phosphate buffer, pH 7, 100–1000 $\mu$mol/l, preferably 400 $\mu$mol/l, FAD, 200–600 $\mu$mol/l, preferably 400 $\mu$mol/l, potassium hexacyanoferrate and 3.5–5 mmol/l, preferably 4 mmol/l, NADH or NADPH. It is possible with the reagent according to the invention to determine nitrate quantitatively over a wide concentration range (0.5 to >100 mg/l nitrate) in a wide variety of matrices, in some cases without sample preparation. It is possible to construct a calibration plot by inclusion of nitrate standard solutions. Complete reduction of the amount of nitrate to be determined is unnecessary. Any interfering secondary activities of the enzyme preparation, such as, for example, nitrite reductase activities and "NAD(P)H oxidase" activities, are likewise unimportant in the kinetic method described. Thus a biochemical reagent for the quantitative determination of nitrate is now available. Another advantage of the reagent according to the invention is the possibility of using NADH in place of the very costly and less soluble NADPH. Quantitative determination of nitrate can be carried out with the method described within a few minutes at room temperature. Other biochemical methods require distinctly longer analysis times.

Example 1

Preparation of nitrate reductase a) Culture and harvesting of the cells

Yeast cells (*Candida boidinii*, DSM 70 026) for obtaining nitrate reductase are cultivated in a completely synthetic medium with potassium nitrate as the sole nitrogen source via the stages 10 ml shake tube, 200 ml conical flask, 10 l fermenter and 100 l fermenter. After a running time of 26 hours in the 100 l fermenter, the cells are separated from the medium and washed with cold buffer A. (Buffer A: potassium phosphate buffer, 0.1 mol/l, pH 7.5, containing 1 mmol/l EDTA, 0.1 mmol/l mercaptoethanol, 4 $\mu$mol/l FAD, 20 $\mu$mol/l potassium hexacyanoferrate.

The yield is 8.6 kg of yeast cells (fresh weight).

The composition of the completely synthetic medium is as follows:
0.04 g/l m-inositol,
1.0 g/l potassium dihydrogen phosphate,
1.0 g/l magnesium sulfate,
4.5 g/l potassium hydrogen tartrate,
1.5 g/l potassium nitrate,
20.0 g/l glucose Trace elements: $AlCl_3$ 2 mg/l, $H_3BO_3$ 2 mg/l, $CuSO_4 \times 5\ H_2O$ 1 mg/l, $FeCl_3 \times 6\ H_2O$ 2 mg/l, KH tartrate 20 mg/l, KI 1 mg/l, $Na_2MoO_4 \times 2\ H_2O$ 2 mg/l, $ZnSO_4 \times 7\ H_2O$ 2 mg/l Vitamins: 4-aminobenzoic acid 0.2 mg/l, biotin 0.02 mg/l, folic acid 0.02 mg/l, nicotinic acid 1 mg/l, Ca D-pantothenate 1 mg/l, pyridoxolium chloride 1 mg/l, riboflavin 0.5 mg/l, thiamine dichloride 0.5 mg/l. The pH is adjusted to 5.0 with sodium hydroxide solution.

b) Preparation of cell-free extracts 2.5 kg of the cells obtained in this way are suspended in 4.5 l of buffer B (buffer A +0.1 mmol/l protease inhibitor, for example PMSP) and disrupted in a glass bead mill.

Disruption conditions: glass beads of diameter 0.5–0.7 mm, 80–85% packing with glass beads, 2000 rpm, throughput 10 l/h, temperature during disruption <10° C. The cell detritus is then removed by centrifugation ($15000 \times g/30$ min). measurement on 4.5 l of crude extract shows a total volume-based activity of 40 kU and a specific activity of 420 mU NADH-dependent nitrate reductase per mg of protein.

c) Purification of the nitrate reductase by anion exchanger chromatography

The crude extract obtained in the preceding step is diluted with buffer B to a conductivity <8 mS and, without interpolation of a nucleic acid precipitation or a fractional neutral salt precipitation, is directly chromatographed on an anion exchanger column (Fractogel EMD TMAE-650 (M)). The column is equilibrated with buffer B beforehand. Active nitrate reductase is eluted with an increasing KCl gradient in buffer B in the region of 140 mmol/l KCl. Active fractions are combined and mixed with 10–50% bovine serum albumin or comparable proteins, and the nitrate reductase is concentrated by ultrafiltration on a membrane (exclusion limit 30 000 Dalton). The solution obtained in this way has a volume of 500 ml and a specific nitrate reductase activity of 7 U/mg of protein. The total activity is 23 kU (yield 57%). Comparable yields are obtained with Hansenula ceferrii (DSM 70 780) and Hansenula saturnus (DSM 70 278) yeast cells as starting materials.

d) Fluidized bed granulation and tableting

The concentrated nitrate reductase fraction is applied in a fluidized bed granulation process to a prepared carrier (mannitol/polyethylene glycol/polyvinylpyrrolidone). The enzyme granules prepared in this way (2.4 kg) contain 7 units of nitrate reductase per gram of granules. The granules are compressed without further additives in a tablet mold and stored at −20° C.

Example 2

Method for determining nitrate

Reagents

1) Reagent mixture: 50 mmol/l potassium phosphate buffer, pH 7.0 20 μmol/l FAD
20 μmol/l $K_3[Fe(CN)_6]$ in fluidized bed granulated form.

2) NADH tablets after fluidized bed granulation on mannitol seeds (1.413 mg of NADH per tablet)

3) Nitrate reductase tablets after fluidized bed granulation (0.7 units of nitrate reductase/tablet)

4) Nitrite color reagent: 97 mg of sulfanilic acid 3 mg of N-(1-naphthyl)ethylenediammonium chloride 5) Nitrate standard solution (100 mg/l)

Preparation of the sample solutions 1. For determination of the blank:

Demineralized water is used as sample solution. 2. To construct a calibration plot:

The standard solution containing 100 mg/l nitrate is diluted with demineralized water to give the required calibration solutions.

Variant 1 contains 20/40/60/80/100 mg/l nitrate standard

Variant 2 contains 2/4/6/8/10 mg/l nitrate standard

Before the measurement, the samples are clarified by filtration and, where appropriate, diluted with demineralized water.

Preparation of the reaction solution (for 10 single determinations):

|  | Variant 1 (5–100 mg/l) | Variant 2 (0.5–10 mg/l) |
| --- | --- | --- |
| Reagent No. | | |
| 1 | 100 mg | 200 mg |
| 2 | 1 tablet | 1 tablet |
| 3 | 1 tablet | 1 tablet |
| dissolve in demineralized water: | 9 ml | 15 ml |
| Determination procedure: | | |
| Conditions/single determination | | |
| Reaction solution | 0.9 ml | 1.5 ml |
| Reaction started by addition of sample solution | 0.1 ml | 0.5 ml |
| Reaction time | 7 min | about 20 min |
| Reaction stopped by addition of Reagent 4 | 100 mg | 100 mg |
| Dilution with water | +2 ml | none |

After Reagent 4 has settled, the extinctions at 540 nm or 525 nm are determined for the supernatant from standards and the samples with the blank as reference.

Evaluation a) using a calibration plot b) $E_{sample}$: $E_{standard}$ = conc.$_{sample}$: conc.$_{standard}$

Example 3

Samples of drinking water are employed directly for the test. Beer samples and other beverages containing carbon dioxide are shaken to remove the carbon dioxide. Fruit juices and other cloudy samples are centrifuged and filtered.

5 g of milk are mixed with 20 ml of 50% strength trichloroacetic acid, adjusted to pH 7 with sodium hydroxide solution, transferred into a 100 ml graduated flask and made up to the mark with water. The clear filtrate after centrifugation and filtration is employed for the test.

About 5 g of meat or meat products from a well-homogenized sample are weighed into a glass beaker, mixed with 20 ml of 50% strength trichloroacetic acid solution and 30 ml of water and homogenized once again in a mixer. The pH is then adjusted to 7.0 with sodium hydroxide solution (2 mol/l), 5 ml of petroleum spirit are added and, after mixing, the mixture is transferred into a 100 ml graduated flask. Water is added until the petroleum spirit layer is completely above the mark. After careful mixing and after phase separation, the petroleum spirit layer is aspirated off.

The aqueous phase is filtered through a fluted filter and employed for the test.

Sample preparation in the case of vegetables, fruit and lettuce entails preparation of an expressed juice, which is then centrifuged and filtered. A solution appropriately diluted with water is employed for the test.

Nitrate determinations in analogy to Example 2 are carried out with the samples prepared in this way. The following table contains typical measurements and the recovery rates.

| Sample | Nitrate concentration (mg/l) | Recovery (%) (mixing test with 50% (v/v) sample, 50% (v/v) standard |
| --- | --- | --- |
| Potatoes | 270 | 99 |
| Onions | 24 | 102 |
| Yellow paprika | 35 | 95 |
| Cucumbers | 41 | 96 |
| Beer | 7 | 96 |
| Mineral water | 2 | 99 |
| Pineapple juice | 11 | 101 |
| Orange juice | 5 | 101 |
| Lettuce | 1700 | 96 |

We claim:

1. An isolated NAD(P)H-dependent nitrate reductase, having a molecular weight in the native state of about 350,000 D, as measured by gel permeation chromatography, of the E. C. 1.6.6.2 type, obtained by a process comprising:

cultivating yeast cells in a synthetic medium comprising nitrate as the sole nitrogen source wherein the yeast cells are of the genera Candida or Hansenula;

disrupting said cells in a phosphate buffer having a pH of about 6.5 to about 8.5, in the presence of a complexing agent, mercaptoethanol, FAD, potassium hexacyanoferrate and a protease inhibitor, to form a cell extract;

removing cell debris from said cell extract by centrifugation, the debris produced by said disrupting;

chromatographing said cell extract on an anion exchange material to obtain fractions comprising nitrate reductase;

mixing said fractions with about 10% to about 50% protein;

concentrating said fractions by ultrafiltration; and drying said concentrated fractions by fluidized bed granulation.

2. An NAD(P)H-dependent nitrate reductase according to claim 1, having the following $K_M$ values:

| NADH | $7.2 \times 10^{-5}$ M |
| --- | --- |
| NADPH | $6.9 \times 10^{-5}$ M |
| $KNO_3$(NADH) | $4.0 \times 10^{-3}$ M |

| -continued | |
|---|---|
| KNO₃(NADPH) | $4.0 \times 10^{-4}$ M. |

3. An NAD(P)H-dependent nitrate reductase according to claim 1, wherein the synthetic nutrient medium contains essentially:
0.04 g/l m-inositol,
1.0 g/l potassium dihydrogen phosphate,
1.0 g/l magnesium sulfate,
4.5 g/l potassium hydrogen tartrate,
1.5 g/l potassium nitrate, and
20.0 g/l glucose.

4. A process for the preparation of an NAD(P)H-dependent nitrate reductase comprising:
cultivating yeast cells, wherein the yeast cells are of the genera Candida or Hansenula, in a synthetic medium comprising nitrate as the sole nitrogen source;
disrupting said cells in a phosphate buffer having a pH of about 6.5 to about 8.5, in the presence of a complexing agent, mercaptoethanol, FAD, potassium hexacyanoferrate, and a protease inhibitor, to form a cell extract;
removing cell debris from said cell extract by centrifugation, the debris produced by said disrupting;
chromatographing said cell extract on an anion exchange material to obtain fractions comprising nitrate reductase;
mixing said fractions with about 10% to about 50% protein;
concentrating said fractions by ultrafiltration; and
drying said concentrated fractions by fluidized bed granulation.

5. A process according to claim 4, wherein the yeast cells are *Candida boidinii*.

6. A reagent for determining nitrate content, comprising a nitrate reductase according to claim 1, NAD(P)H, and a color reagent for determining nitrite.

7. A process according to claim 4, wherein the synthetic medium consists essentially of 0.04 g/l m-inositol, 1.0 g/l potassium dihydrogen phosphate, 1.0 g/l magnesium sulfate, 4.5 g/l potassium hydrogen tartrate, 1.5 g/l potassium nitrate, and 20.0 g/l glucose.

8. An isolated NAD(P)H-dependent nitrate reductase of the EC 1.6.6.2 type, having $K_m$ values of $7.2 \times 10^{-5}$M for NADH, of $6.9 \times 10^{-5}$M for NADPH, of $4.0 \times 10^{-3}$M for KNO₃(NADH), of $4.0 \times 10^{-4}$ for KNO₃(NADPH), obtained by a process according to claim 4.

9. An isolated NAD(P)H-dependent nitrate reductase obtained by a process according to claim 4, wherein:
the yeast cells are *Candida boidinii*, and
the nitrate reductase is of the EC 1.6.6.2 type and has a molecular weight in the native state of about 350,000 D, as measured by gel permeation chromatography, and $K_m$ values of $7.2 \times 10^{-5}$M for NADH, of $6.9 \times 10^{-5}$M for NADPH, of $4.0 \times 10^{-3}$M for KNO₃(NADH), of $4.0 \times 10^{-4}$ for KNO₃(NADPH).

10. A reagent kit for determining nitrate content, comprising the nitrate reductase obtained by a process according to claim 4, NAD(P)H, and a color reagent for determining nitrite content.

11. A process for the preparation of an NAD(P)H-dependent nitrate reductase comprising:
cultivating yeast cells in a synthetic medium comprising nitrate as the sole nitrogen source wherein the yeast cells are of the genera Candida or Hansenula;
disrupting said cells in a phosphate buffer having a pH of about 6.5 to about 8.5, in the presence of a complexing agent, mercaptoethanol, FAD, potassium hexacyanoferrate, and a protease inhibitor, to form a cell extract;
removing cell debris from said cell extract by centrifugation, the debris produced by said disrupting;
chromatographing said cell extract, obtained directly from said centrifugation, on an anion exchange material to obtain fractions comprising nitrate reductase;
mixing said fractions obtained directly from said chromatography with about 10% to about 50% protein;
concentrating by ultrafiltration said fractions obtained directly after mixing; and
drying said concentrated fractions by fluidized bed granulation.

* * * * *